United States Patent
Lee et al.

(10) Patent No.: US 10,258,663 B2
(45) Date of Patent: Apr. 16, 2019

(54) METHOD FOR TREATING MALIGNANT PLEURAL EFFUSION

(71) Applicant: Chen-Yu Lee, Taipei (TW)

(72) Inventors: Chen-Yu Lee, Taipei (TW); Tsai-Wang Huang, Taipei (TW); Yan-Chih Liao, Taipei (TW)

(73) Assignee: Chen-Yu Lee, Taipei (TW)

( * ) Notice: Subject to any disclaimer, the term of this patent is extended or adjusted under 35 U.S.C. 154(b) by 126 days.

(21) Appl. No.: 15/668,830

(22) Filed: Aug. 4, 2017

(65) Prior Publication Data

US 2019/0038698 A1    Feb. 7, 2019

(51) Int. Cl.

| | |
|---|---|
| *A61K 36/00* | (2006.01) |
| *A61K 36/8988* | (2006.01) |
| *A61K 36/076* | (2006.01) |
| *A61K 36/07* | (2006.01) |
| *A61K 36/284* | (2006.01) |
| *A61K 36/884* | (2006.01) |
| *A61K 36/31* | (2006.01) |
| *A61K 36/17* | (2006.01) |
| *A61K 36/734* | (2006.01) |
| *A61K 36/77* | (2006.01) |
| *A61K 36/71* | (2006.01) |
| *A61K 36/258* | (2006.01) |
| *A61K 36/47* | (2006.01) |
| *A61K 36/83* | (2006.01) |
| *A61K 36/88* | (2006.01) |
| *A61K 35/32* | (2015.01) |

(52) U.S. Cl.
CPC .......... *A61K 36/8988* (2013.01); *A61K 35/32* (2013.01); *A61K 36/07* (2013.01); *A61K 36/076* (2013.01); *A61K 36/17* (2013.01); *A61K 36/258* (2013.01); *A61K 36/284* (2013.01); *A61K 36/31* (2013.01); *A61K 36/47* (2013.01); *A61K 36/71* (2013.01); *A61K 36/734* (2013.01); *A61K 36/77* (2013.01); *A61K 36/83* (2013.01); *A61K 36/88* (2013.01); *A61K 36/884* (2013.01)

(58) Field of Classification Search
CPC ..................................................... A61K 36/00
See application file for complete search history.

(56) References Cited

FOREIGN PATENT DOCUMENTS

CN    1709309 A  * 12/2005

OTHER PUBLICATIONS

Chen-Yu Lee et al., "Clinical Treatment of Malignant Pleural Effusion (Suspended Rheum) with on Cold Damage and Miscellaneous Diseases Shi Zao Tang Pattern Types, and Related Topics", English abstract, pp. 1-2, The Journal of Chinese-Western Neurological Medicine, Dec. 18, 2016.

* cited by examiner

*Primary Examiner* — Qiuwen Mi
(74) *Attorney, Agent, or Firm* — Bacon & Thomas, PLLC

(57) ABSTRACT

The present invention is directed to a method for treating malignant pleural effusion comprising administering a first herbal medicine composition to a subject in need; wherein the first chinese herbal medicine is an extract of a first mixture comprising *Poria, Grifola, Rhizoma Atractylodis, Rhizoma Alismatis, Semen Lepidii, Rhizoma Atractylodis* Macrocephalae, Herba Ephedrae, Fructus Jujubae, *Fructus Crataegi*, dried Langan, *Radix* Stephaniae Tetrandrae, and *Rhizoma* Gastrodiae; *Ginseng* powder; and a second mixture comprising *Radix Kansui, Euphorbia pekinensis, Flos Genkwa*.

17 Claims, No Drawings

METHOD FOR TREATING MALIGNANT PLEURAL EFFUSION

BACKGROUND OF THE INVENTION

1. Field of the Invention

The present invention relates to a method for treating pleural effusion and, more particularly, to a method for treating malignant pleural effusion, comprising administering an effective amount of an chinese herbal medicine to achieve an object of treating or ameliorate pleural effusion.

2. Description of Related Art

As the potential of chinese herbal medicine for treating cancer, chinese herbal medicine has drawn public's attention in recent years. The principle of chinese herbal medicine application is based on the practice of traditional Chinese medicine theory.

Normally, there is 3-15 mL fluid retained in the human chest, and it has a lubricant function when breathing; however, the amount of the fluid in the chest is not fixed, but in a dynamic balance. Breaking the balance will result in forming the fluid too fast or absorbing the fluid too slow, and thus producing pleural effusion.

Pleural effusion can be divided into two categories, transudative and exudative pleural effusion, according to the causes. Transudative pleural effusion is commonly caused by systemic disease or certain organ disease, such as heart failure, kidney failure or cirrhosis. Usually pleural effusion happens on the both sides of the chest simultaneously. Exudative pleural effusion is usually caused by lung disease, such as pneumonia, pulmonary tuberculosis and the like, or by cancer, such as lung cancer, breast cancer and the like; and pleural effusion happens on the one side of the chest mostly.

Common symptoms of pleural effusion are cough, dyspnea, chest pain, easy to pant, and weakened respiration, severe cases will be accompanied with trachea to the contralateral displacement, or need of an oxygen generator to assist in breath.

Patients with non-malignant pleural effusion can significantly ameliorate or cure pleural effusion by discharging the fluid and treating the primary disease simultaneously; however, patients with malignant pleural effusion can only ameliorate or reduce the occurrence of pleural effusion since it is difficult to cure tumors. Drainage is a common way to discharge the fluid in the chest, and it can achieve the goal of discharging the fluid quickly. However, drainage alone cannot cure pleural effusion completely, after all, it is just a very effective adjuvant therapy, and the patient may continually produce the fluid in the chest; also, administering drainage in a short period of time may cause irreversible damages to the patient. Therefore, for patients with malignant pleural effusion, it is desired to treat pleural effusion with a safer or long-term treatment.

SUMMARY OF THE INVENTION

One of the objects of the present invention is to provide a method for treating malignant pleural effusion. The method for treating malignant pleural effusion comprises administering a first chinese herbal medicine, which can ameliorate or treat pleural effusion, to a subject in need; also, it can be a safer or long-term use for administering to patients with a tumor or elderly patients since it is not necessary to conduct a drainage surgery and is a non-invasive treatment; in addition, the method in the present invention provides a new treatment for the patients who are not suitable for receiving a surgery.

The present invention may further comprise administering a second chinese herbal medicine to a subject in need. The second chinese herbal medicine comprises the powder of Zhibai Dihuang Decoction, Yeh Gan Ma Hwang Tang, Ginseng, and Velvet Antler; wherein Zhibai Dihuang Decoction is traditionally used to treat yin-vacuity fire efflux, dry mouth, and sore throat, nowadays, it can also be used to treat chronic pharyngitis, acute urinary tract infection and the like; Yeh Gan Ma Hwang Tang can be used to diffuse the lung and transform phlegm, relieve asthma, relieve cough and the like, and it can be clinically applied to asthmatic bronchitis, chronic bronchitis and the like. Preferably, the second mixture is the powders comprising *Radix Kansui, Euphorbia pekinensis, Flos Genkwa*.

The method for treating malignant pleural effusion of the present invention comprises administering a first chinese herbal medicine to a subject in need;

wherein the first chinese herbal medicine is an extract of a first mixture comprising *Poria, Grifola* (Chuling), *Rhizoma Atractylodis* (*Atractylodes lancea*), *Rhizoma Alismatis* (*Alisma plantago-aquatica*), *Semen Lepidii* (Seed of Pepperweed), *Rhizoma Atractylodis* Macrocephalae (*Atractylodes macrocephala*), Herba Ephedrae (Ephedra), Fructus Jujubae (Chinese red date), *Fructus Crataegi* (Chinese Hawthorn), dried Longan, *Radix* Stephaniae Tetrandrae (*Stephania tetrandra*), and *Rhizoma* Gastrodiae (*Gastrodia elata*); Ginseng powder; and a second mixture comprising *Radix Kansui* (*Euphorbia kansui*), *Euphorbia pekinensis,* and *Flos Genkwa* (*Daphne genkwa*).

Preferably, the first mixture comprises 6-10 parts by weight of *Poria*, 6-10 parts by weight of *Grifola*, 6-10 parts by weight of *Rhizoma Atractylodis*, 13-17 parts by weight of *Rhizoma Alismatis*, 13-17 parts by weight of *Semen Lepidii*, 6-10 parts by weight of *Rhizoma Atractylodis* Macrocephalae, 1-5 parts by weight of Herba Ephedrae, 5-10 parts by weight of Fructus Jujubae, 2-6 parts by weight of *Fructus Crataegi*, 6-10 parts by weight of dried Longan, 2-6 parts by weight of *Radix* Stephaniae Tetrandrae, and 6-10 parts by weight of *Rhizoma* Gastrodiae; more preferably, the first mixture comprises 7-9 parts by weight of *Poria*, 7-9 parts by weight of *Grifola*, 7-9 parts by weight of *Rhizoma Atractylodis*, 14-16 parts by weight of *Rhizoma Alismatis*, 14-16 parts by weight of *Semen Lepidii*, 7-9 parts by weight of *Rhizoma Atractylodis* Macrocephalae, 2-4 parts by weight of Herba Ephedrae, 6-9 parts by weight of Fructus Jujubae, 3-5 parts by weight of *Fructus Crataegi*, 7-9 parts by weight of dried Longan, 3-5 parts by weight of *Radix* Stephaniae Tetrandrae, and 7-9 parts by weight of *Rhizoma* Gastrodiae. Preferably, the part by weight of the first mixture is 3.75 gram per part.

The amount of the *Ginseng* powder in the first chinese herbal medicine used in the present invention is not particularly limited, preferably 1-5 parts by weight, more preferably 2-4 parts by weight. Preferably, the part by weight of the *Ginseng* powder is 3.75 grams per part.

The weight ratio of the second mixture of the first chinese herbal medicine used in the present invention is not particularly limited, preferably 0.5-1.5:0.5-1.5:0.5-1.5 (*Radix Kansui:Euphorbia pekinensis:Flos Genkwa*), more preferably 0.8-1.2:0.8-1.2:0.8-1.2 (*Radix Kansui:Euphorbia pekinensis:Flos Genkwa*).

The preparation of the first chinese herbal medicine comprises: providing the first mixture; mixing the first mixture and water to form a third mixture; decocting the third mixture to obtain a crude extract; filtering the crude extract to remove a residue and obtain a liquid extract; and adding the *Ginseng* powder and the second mixture to the liquid extract in order to obtain the first chinese herbal medicine.

The amount of water used to form the third mixture in the present invention preferably is 425-535 parts by weight, more preferably 450-500 parts by weight. Preferably, the part by weight of the water is 3.75 grams per part.

The method for treating malignant pleural effusion of the present invention may further comprise administering a second chinese herbal medicine to a subject in need; wherein the second chinese herbal medicine is the powder of a fourth mixture comprising Zhibai Dihuang Decoction, Yeh Gan Ma Hwang Tang, *Ginseng,* and Velvet antler.

The fourth mixture used in the present invention preferably comprises 0.5-4 parts by weight of Zhibai Dihuang Decoction, 0.1-2 parts by weight of Yeh Gan Ma Hwang Tang, 0.1-2 parts by weight of *Ginseng*, and 0.05-1.5 parts by weight of Velvet Antler; more preferably 1-3 parts by weight of Zhibai Dihuang Decoction, 0.5-1.5 parts by weight of Yeh Gan Ma Hwang Tang, 0.5-1.5 parts by weight of *Ginseng,* and 0.1-1 parts by weight of Velvet Antler. Preferably, the part by weight of the fourth mixture is 3.75 grams per part.

The method of decoction used in the present invention is not particularly limited, and may be carried out by any method known in the art. The method of "drying" used herein is not particularly limited and may be carried out using any method known in the art, such as baking dry.

Other objects, advantages, and novel features of the invention will become more apparent from the following detailed description.

DETAILED DESCRIPTION OF THE PREFERRED EMBODIMENT

Ordinal numbers such as "first", "second", "fourth" and the like used in the specification and claim for modifying elements of the claim do not mean and represent the claimed elements have any antecedent ordinal number, nor do they represent the order (or order of production) between a claimed element and another claimed element. The ordinal numbers are only used to clearly distinguish certain claimed elements having the same name.

Unless specified otherwise, all technical and scientific terms set forth in the specification and claims of the present invention are defined as follows. The singular term "a", "an", or "the", unless specified otherwise, refers to more than one object. The term "or" or "and" used herein, unless specified otherwise, refers to "and/or". In addition, the term "include" or "comprise" used herein are open ended conjunctions. The preceding paragraphs are merely systematic references and should not be construed as limiting the subject matter of the invention. Unless specified otherwise, the materials used herein are commercially available, and the ways to get materials listed below are merely exemplary.

Preparation Example 1: Preparation of an Extract of the First Mixture

Eight parts by weight of *Poria,* 8 parts by weight of *Grifola,* 8 parts by weight of *Rhizoma Atractylodis,* 15 parts by weight of *Rhizoma Alismatis,* 15 parts by weight of *Semen Lepidii,* 8 parts by weight of *Rhizoma Atractylodis* Macrocephalae, 3 parts by weight of Herba Ephedrae, 8 parts by weight of Fructus Jujubae, 4 parts by weight of *Fructus Crataegi,* 8 parts by weight of dried Longan, 4 parts by weight of *Radix* Stephaniae Tetrandrae, and 8 parts by weight of *Rhizoma* Gastrodiae were provided with 480 parts by weight of water to form about 120 parts by weight of a crude extract; then filter the crude extract to remove a residue and obtain an extract of a first mixture.

Preparation Example 2: Preparation of a Second Mixture

*Radix Kansui, Euphorbia pekinensis* and *Flos Genkwa* were provided, dried, and co-grinded in a weight ratio of about 1:1:1 to produce about 100 grams powder, thereafter, a second mixture was obtained.

Preparation Example 3: Preparation of a First Chinese Herbal Medicine

The extract of the first mixture was provided, and then added with *Ginseng* powder and the second mixture to obtain the first chinese herbal medicine.

Preparation Example 4: Preparation of a Fourth Mixture

Two parts by weight of Zhibai Dihuang Decoction, 1 parts by weight of Yeh Gan Ma Hwang Tang, 1 parts by weight of *Ginseng,* and 0.5 parts by weight of Velvet Antler were provided, and then mixed to obtain a fourth mixture.

Embodiment 1

The patient's symptoms in the Embodiment 1 were panting for light intensity activities and dramatic decrease in weight from 44 kg to 38 kg; after examination, it was found that pleural effusion shown in the right lung, and it might be malignant tumor according to computed tomography (CT) and magnetic resonance imaging (MRI) report; after lung aspiration, the patient started to pant within a week.

The treatment for the patient in the present embodiment comprises: on the first day, 1.6 g of the second mixture and 2.8 parts by weight of *Ginseng* powder were added to the extract of the first mixture and then divided into aliquots for ter in die administration; from day 2, the extract of the first mixture was administered together with 3 parts by weight of *Ginseng* powder. After two weeks, there was no pleural effusion found according to the X-ray film.

Embodiment 2

The patient in the Embodiment 2 was about 90 years old, and the patient's symptoms were cough, panting for light intensity activities and weak knees (the patient suddenly fell down during a slow-walking); the patient was diagnosed to have a pleural effusion and malignant lung tumor, and relied on oxygen generator to breathe. After lung aspiration, symptoms recurred within a week.

The treatment for the patient in the Embodiment 2 comprises: on the first day, 1.3 g of the second mixture and 3 parts by weight of *Ginseng* powder were added to an extract of the first mixture, and then divided into aliquots for ter in die administration. From day 2, 3 parts by weight of *Ginseng* powder was added to the extract of the first mixture, and then divided into aliquots for ter in die administration. After two weeks, there was no pleural effusion shown according to the X-ray film. After consecutive intake of the extract of the first mixture for about 40 days, the patient's symptom of pant was ameliorated significantly; however, the patient still coughed for dozens times and had sleeping difficulties every day, therefore, all of the aforementioned administration was stopped, and 10 g of the fourth mixture was administered to the patient once per day; and the patient barely coughed and slept well after three days.

Embodiment 3

The patient in the Embodiment 3 was 92 years old, and the patient's symptoms were cough, sudden weight loss, and panting for light intensity activities (even lying). The patient was diagnosed to have a pleural effusion in the right lung and malignant lung tumor, and relied on oxygen generator to breathe. After 200 mL fluid was aspired from the lung, the symptoms recurred within a week.

The treatment for the patient in the Embodiment 3 comprises: on the first day, 1.5 g of the second mixture and 3 parts by weight of *Ginseng* powder were added to an extract of the first mixture, and divided into aliquots for ter in die administration. From day 2, 3.5 parts by weight of *Ginseng* powder was added to the extract of the first mixture, and then divided into aliquots for ter in die administration. After two weeks, there was no pleural effusion shown according to the X-ray film. After consecutive intake of the first mixture for about 40 days, the patient's symptom of pant was ameliorated significantly, and the patient was able to do light intensity activities; however, the patient still coughed up sputum for dozens times every day, therefore, from day 41, all of the aforementioned administration was stopped, and 10 g of the powder of the fourth mixture was administered to the patient twice per day; on day 43, about 12-15 g of the powder of the fourth mixture was administered to the patient; thereafter, it was found that the patient barely coughed and panted, and did not need to rely on the oxygen generator to breathe.

Although the present invention has been explained in relation to its preferred embodiment, it is to be understood that many other possible modifications and variations can be made without departing from the spirit and scope of the invention as hereinafter claimed.

What is claimed is:

1. A method for treating malignant pleural effusion comprising:
   administering a first chinese herbal medicine to a subject in need;
   wherein the first chinese herbal medicine is an extract of a first mixture comprising *Poria, Grifola, Rhizoma Atractylodis, Rhizoma Alismatis, Semen Lepidii, Rhizoma Atractylodis* Macrocephalae, Herba Ephedrae, Fructus Jujubae, *Fructus Crataegi,* dried Longan, *Radix* Stephaniae Tetrandrae, and *Rhizoma* Gastrodiae; *Ginseng* powder; and
   a second mixture comprising *Radix Kansui, Euphorbia pekinensis, Flos Genkwa.*

2. The method as claimed in claim 1, wherein a preparation of the first chinese herbal medicine comprises:
   providing the first mixture;
   mixing the first mixture and water to form a third mixture;
   decocting the third mixture to obtain a crude extract;
   filtering the crude extract to remove a residue and obtain a liquid extract; and
   adding the *Ginseng* powder and the second mixture to the liquid extract in order to obtain the first chinese herbal medicine.

3. The method as claimed in claim 1, wherein the first mixture comprises 6-10 parts by weight of *Poria,* 6-10 parts by weight of *Grifola,* 6-10 parts by weight of *Rhizoma Atractylodis,* 13-17 parts by weight of *Rhizoma Alismatis,* 13-17 parts by weight of *Semen Lepidii,* 6-10 parts by weight of *Rhizoma Atractylodis* Macrocephalae, 1-5 parts by weight of Herba Ephedrae, 5-10 parts by weight of Fructus Jujubae, 2-6 parts by weight of *Fructus Crataegi,* 6-10 parts by weight of dried Longan, 2-6 parts by weight of *Radix* Stephaniae Tetrandrae, and 6-10 parts by weight of *Rhizoma* Gastrodiae.

4. The method as claimed in claim 3, wherein the part by weight of the first mixture is 3.75 grams per part.

5. The method as claimed in claim 4, wherein the first mixture comprises 7-9 parts by weight of *Poria,* 7-9 parts by weight of *Grifola,* 7-9 parts by weight of *Rhizoma Atractylodis,* 14-16 parts by weight of *Rhizoma Alismatis,* 14-16 parts by weight of *Semen Lepidii,* 7-9 parts by weight of *Rhizoma Atractylodis* Macrocephalae, 2-4 parts by weight of Herba Ephedrae, 6-9 parts by weight of Fructus Jujubae, 3-5 parts by weight of *Fructus Crataegi,* 7-9 parts by weight of dried Longan, 3-5 parts by weight of *Radix Stephaniae Tetrandrae, and* 7-9 parts by weight of *Rhizoma* Gastrodiae.

6. The method as claimed in claim 1, wherein the *Ginseng* powder is 1-5 parts by weight.

7. The method as claimed in claim 6, wherein the part by weight of the *Ginseng* powder is 3.75 grams per part.

8. The method as claimed in claim 6, wherein the *Ginseng* powder is 2-4 parts by weight.

9. The method as claimed in claim 1, wherein the weight ratio of the second mixture is 0.5-1.5;0.5-1.5:0.5-1.5 (*Radix Kansui:Euphorbia pekinensis:Flos Genkwa*).

10. The method as claimed in claim 9, wherein the weight ratio of the second mixture is 0.8-1.2:0.8-1.2;0.8-1.2 (*Radix Kansui:Euphorbia pekinensis:Flos Genkwa*).

11. The method as claimed in claim 2, wherein the water is 425-535 parts by weight.

12. The method as claimed in claim 11, wherein the part by weight of the water is 3.75 gram per part.

13. The method as claimed in claim 1, further comprising a second chinese herbal medicine; wherein the second chinese herbal medicine is a powder of a fourth mixture comprising Zhibai Dihuang Decoction, Yeh Gan Ma Hwang Tang, *Ginseng,* and Velvet Antler.

14. The method as claimed in claim 13, wherein the fourth mixture comprises 0.5-4 parts by weight of Zhibai Dihuang Decoction, 0.1-2 parts by weight of Yeh Gan Ma Hwang Tang, 0.1-2 parts by weight of *Ginseng,* and 0.05-1.5 parts by weight of Velvet Antler.

15. The method as claimed in claim 14, wherein the part by weight of the fourth mixture is 3.75 grams per part.

16. The method as claimed in claim 15, wherein the fourth mixture comprises 1-3 parts by weight of Zhibai Dihuang Decoction, 0.5-1.5 parts by weight of Yeh Gan Ma Hwang Tang, 0.5-1.5 parts by weight of *Ginseng,* and 0.1-1 parts by weight of Velvet Antler.

17. The method as claimed in claim 1, wherein the second mixture are powders comprising *Radix Kansui, Euphorbia pekinensis, Flos Genkwa.*

* * * * *